United States Patent
Ward et al.

(10) Patent No.: US 10,695,071 B2
(45) Date of Patent: Jun. 30, 2020

(54) TOURNIQUET

(71) Applicant: REGENTS OF THE UNIVERSITY OF MICHIGAN, Ann Arbor, MI (US)

(72) Inventors: Kevin R. Ward, Superior Township, MI (US); Albert J. Shih, Ann Arbor, MI (US); Jeffrey Stephen Plott, Algonac, MI (US); Thuan Doan, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 125 days.

(21) Appl. No.: 15/866,528

(22) Filed: Jan. 10, 2018

(65) Prior Publication Data

US 2018/0193030 A1 Jul. 12, 2018

Related U.S. Application Data

(60) Provisional application No. 62/455,205, filed on Jan. 11, 2017.

(51) Int. Cl.
*A61B 17/132* (2006.01)
*A61B 17/00* (2006.01)

(52) U.S. Cl.
CPC ...... *A61B 17/1322* (2013.01); *A61B 17/1325* (2013.01); *A61B 2017/00367* (2013.01)

(58) Field of Classification Search
CPC ............ A61B 17/1322; A61B 17/1325; A61B 17/1327; A61B 2017/00367; A61B 2017/0046
See application file for complete search history.

(56) References Cited

U.S. PATENT DOCUMENTS

| | | | | |
|---|---|---|---|---|
| 1,824,516 A | * | 9/1931 | Tyvand | A61B 17/1322 606/203 |
| 4,036,229 A | * | 7/1977 | Marinello | A61M 35/00 604/289 |
| 6,068,646 A | * | 5/2000 | Lam | A61B 17/1325 606/157 |
| 2012/0053617 A1 | * | 3/2012 | Benz | A61B 17/1325 606/203 |
| 2013/0123836 A1 | * | 5/2013 | Lampropoulos | A61B 17/1325 606/203 |

FOREIGN PATENT DOCUMENTS

| | | |
|---|---|---|
| CN | 204410905 U | 6/2015 |
| GB | 203281 A | 9/1923 |
| WO | WO-2005053506 A2 | 6/2005 |
| WO | WO-2016179976 A1 | 11/2016 |

OTHER PUBLICATIONS

Search Report for International application No. PCT/US18/13062, dated Mar. 28, 2018.
Written Opinion for International application No. PCT/US18/13062, dated Mar. 28, 2018.

* cited by examiner

*Primary Examiner* — Katherine M Rodjom
(74) *Attorney, Agent, or Firm* — Marshall, Gerstein & Borun LLP

(57) ABSTRACT

A portable compact tourniquet includes a pivot housing, a strap carriage that is linearly translatable relative to the pivot housing, and a screw assembly. When the screw assembly is operated, the strap carriage away from the pivot housing, thus tightening a tourniquet strap that is attached to the strap carriage and to the pivot housing.

20 Claims, 8 Drawing Sheets

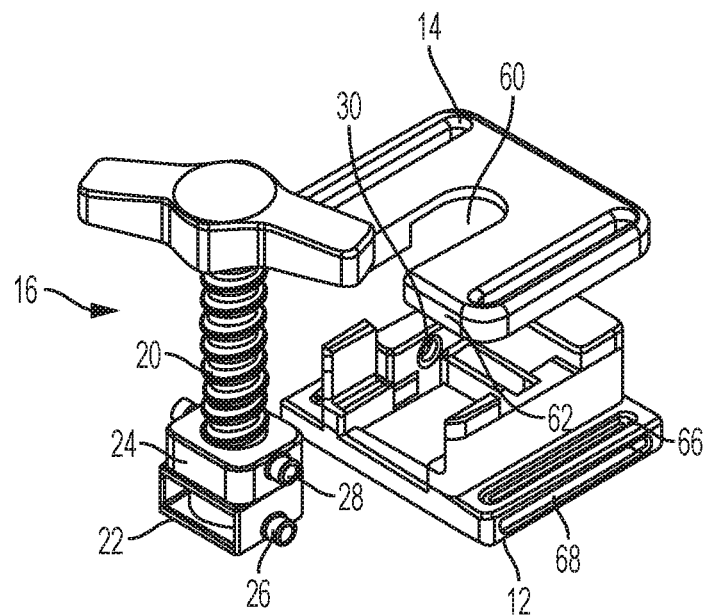
FIG. 4
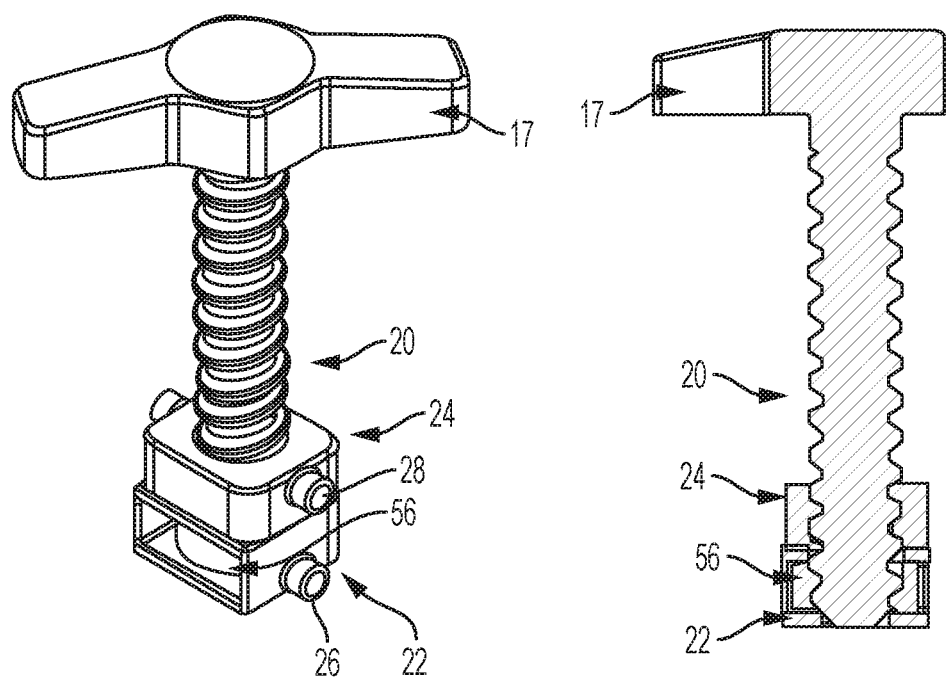
FIG. 5
FIG. 6

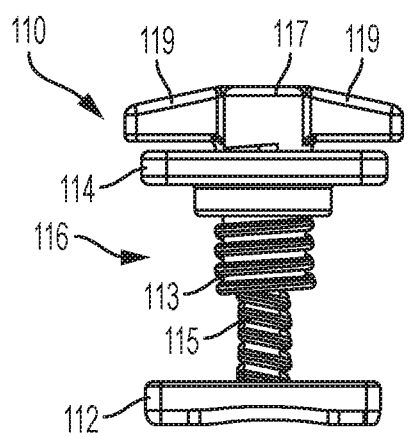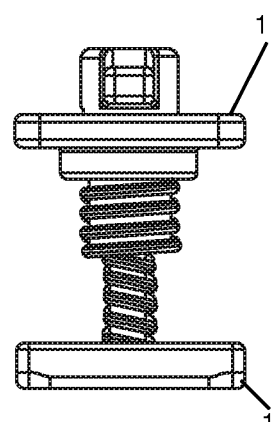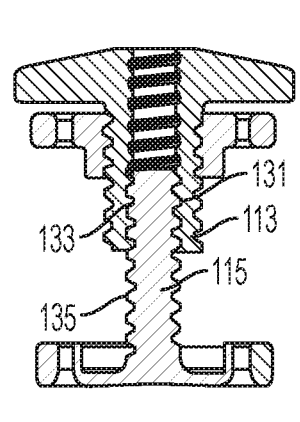
FIG. 12A  FIG. 12B  FIG. 12C
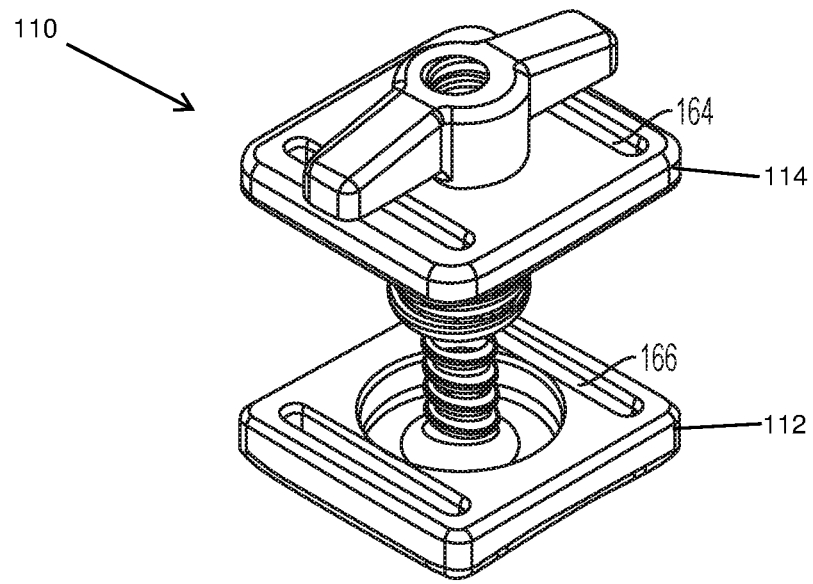
FIG. 13A

TOURNIQUET

FIELD OF THE INVENTION

The invention generally relates to tourniquets and more specifically to portable compact tourniquets.

BACKGROUND OF THE INVENTION

Hemorrhage from vascular injuries in the extremities, such as the arms and legs, can be difficult to treat by a single person. While the treatment of such injuries is challenging when they occur in civilian populations, treatment may be even more difficult in combat situations. Improvements in body armor have reduced mortality from combat injuries to the chest. However, the incidence of injuries to the extremities and the associated mortality rates remain high. Recent efforts have developed better tourniquets for treatment of these extremities wounds.

Controlling hemorrhage by application of direct manual pressure may be particularly challenging in cases where the injured person is alone. In fact, most current tourniquet devices are designed to be applied "one-handed." Because of this, it can be difficult and very painful to achieve a tourniquet pressure that stops blood flow in the limb because of the narrow width of most tourniquet bands.

SUMMARY

In accordance with one exemplary aspect of the present invention, a portable compact tourniquet includes a pivot housing, a strap carriage that is linearly translatable relative to the pivot housing, and a screw assembly that is pivotably attached to the pivot housing. In a deployed condition, the screw assembly moves the strap carriage away from the pivot housing when the screw assembly is operated.

In accordance with another exemplary aspect of the present invention, a portable compact tourniquet includes a screw base, a strap carriage that is linearly translatable relative to the screw base, and a screw assembly that is rotatably connected to the screw base. The screw assembly includes a first screw and a second screw that is nested or telescoped within the first screw.

In further accordance with any one or more of the foregoing aspects, a portable compact tourniquet may further include any one or more of the following preferred forms.

In some preferred forms, the screw assembly may include a screw that is rotatably attached to a housing nut, which is pivotably attached to the pivot housing.

In other preferred forms, the screw assembly may include a riding nut that is movably attached to the screw.

In yet other preferred forms, the housing nut may include a housing pivot and the riding nut may include a riding pivot.

In yet other preferred forms, one of the housing pivot and the riding pivot may include a pair of outwardly extending hubs.

In yet other preferred forms, the pivot housing may include a pair of pivot hub receptacles.

In yet other preferred forms, the pivot hub receptacles are blind bores.

In yet other preferred forms, the strap carriage may include a pair of strap hub receptacles.

In yet other preferred forms, the strap hub receptacles are blind bores having an opening on a bottom side of the strap carriage.

In yet other preferred forms, the strap carriage may include a guide ramp surface that extends away from each strap hub receptacle.

In yet other preferred forms, a centering mechanism may orient the housing nut and the riding nut relative to one another in a closed position.

In yet other preferred forms, the centering mechanism may include a mating boss on one of the riding nut and the housing nut and a mating pocket on the other of the housing nut and the riding nut.

In yet other preferred forms, the screw assembly may include a handle disposed at one end of the screw.

In yet other preferred forms, the handle may include two outwardly extending shoulders.

In yet other preferred forms, the pivot housing may include a pair of support tabs for supporting a bottom of the housing nut.

In yet other preferred forms, the pivot housing may include a shelf for receiving a portion of the housing nut.

In yet other preferred forms, the screw assembly may include a stopping nut that is fixed within the housing nut, the screw being rotatably secured to the stopping nut.

In yet other preferred forms, the strap carriage may have a central slot that extends through a front edge of the strap carriage.

In yet other preferred forms, the strap carriage may have a pair of lateral slots that are configured to receive a tourniquet strap.

In yet other preferred forms, the pivot housing may have a pair of lateral slots that are configured to receive a tourniquet strap.

In yet other preferred forms, the first screw may have a larger diameter than the second screw.

In yet other preferred forms, the first screw may have a hollow central bore with female threads, the female threads cooperating with male threads on an outer surface of the second screw.

BRIEF DESCRIPTION OF THE DRAWINGS

FIG. 4 is an exploded perspective view of the portable compact tourniquet of FIG. 1B.

FIG. 5 is a perspective view of the screw assembly of the portable compact tourniquet of FIG. 1B.

FIG. 6 is a side cross-sectional view of the screw assembly of FIG. 5.

FIG. 12A is a front view of a second embodiment of a portable compact tourniquet, with a screw assembly in an extended position.

FIG. 12B is a side view of the portable compact tourniquet of FIG. 12A.

FIG. 12C is a front cross-sectional view of the portable compact tourniquet of FIG. 12A.

FIG. 13A is a top perspective view of the portable compact tourniquet of FIG. 12A.

DETAILED DESCRIPTION

The disclosed tourniquets achieve blood occlusion in body limbs in emergency situations while enhancing comfort and intuitive use. A screw mechanism in the disclosed tourniquets is non-backdrivable, thus allowing for the tourniquet to hold high pressures with very little user effort to ensure that the supply of blood is interrupted to the wound site.

The tourniquet band may include a nylon strap and strap buckle, which allows for adjustment of diameter for initial pressure and fit. The strap feeds through the tourniquet mechanism which includes the screw assembly, a pivot housing, and a strap carriage. In one embodiment, the screw assembly is positionable in two orientations, one in which the screw assembly folded down for compact storage, and a second where the screw assembly is deployed for use. In the folded down position, the tourniquet strap may be wrapped around the entire tourniquet mechanism assembly for easy storage.

Figure 1A:
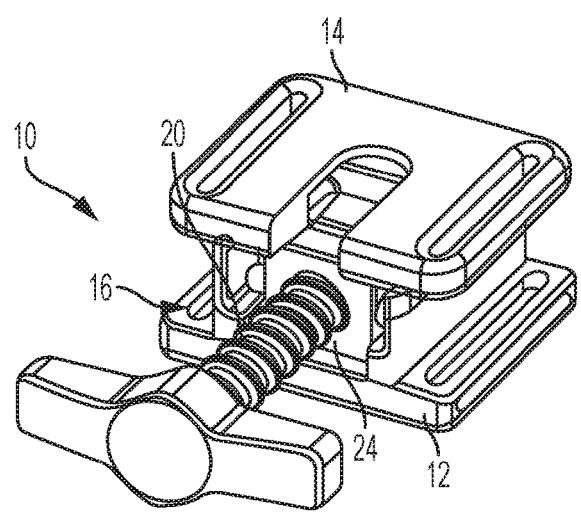
FIG. 1A is a perspective view of a first embodiment of a portable compact tourniquet, with a screw assembly being in a stowed position.
Figure 1B:
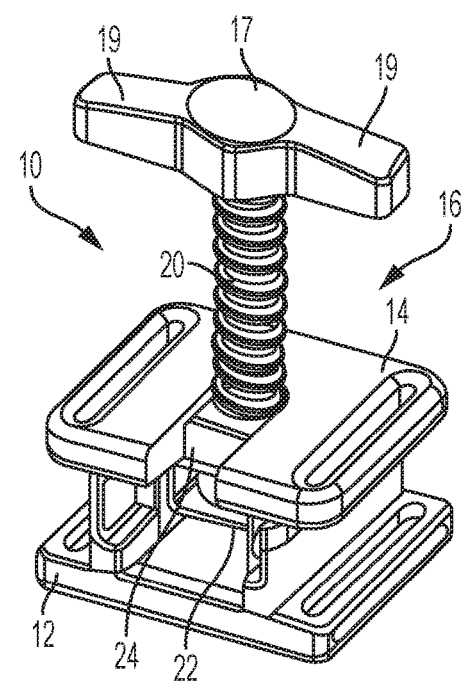
FIG. 1B is a perspective view of the portable compact tourniquet of FIG. 1A, with the screw assembly being in a deployed position.
Figure 2:
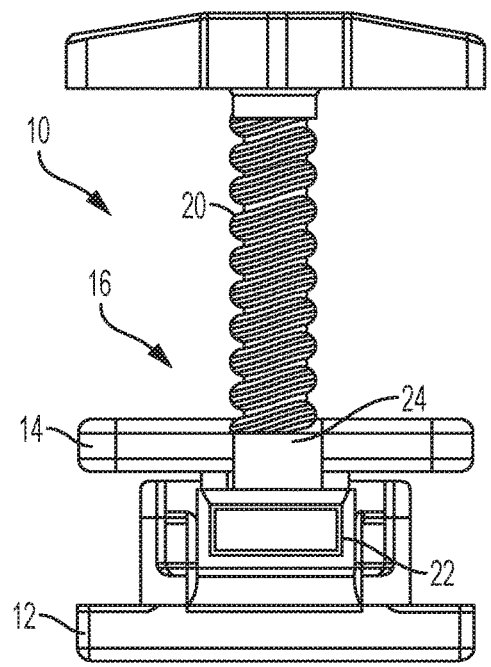
FIG. 2 is a side elevational view of the portable compact tourniquet of FIG. 1B.
Figure 3:
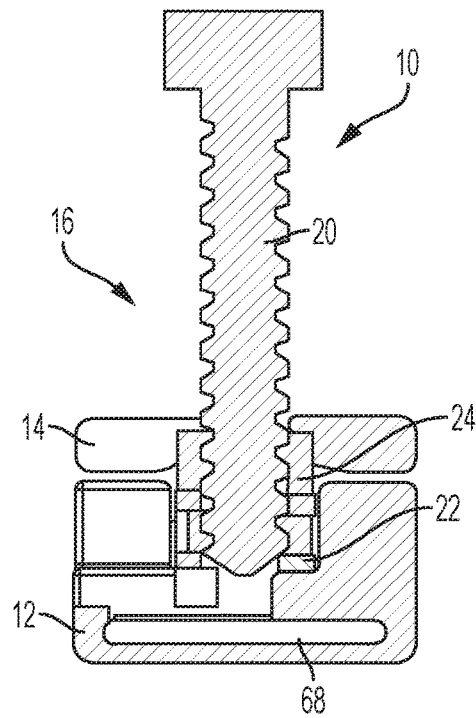
FIG. 3 is a side cross-sectional view of the portable compact tourniquet of FIG. 1B.

Turning now to FIGS. 1-3, one embodiment of a portable compact tourniquet 10 includes a pivot housing 12, a strap carriage 14 that is linearly translatable relative to the pivot housing 12, and a screw assembly 16 that is pivotably attached to the pivot housing 12. In a deployed condition, which is illustrated in FIGS. 1B, 2, and 3, the screw assembly 16 moves the strap carriage 14 away from the pivot housing 12 when the screw assembly 16 is operated, to tighten a tourniquet strap (not shown in FIGS. 1-3).

Figure 10:
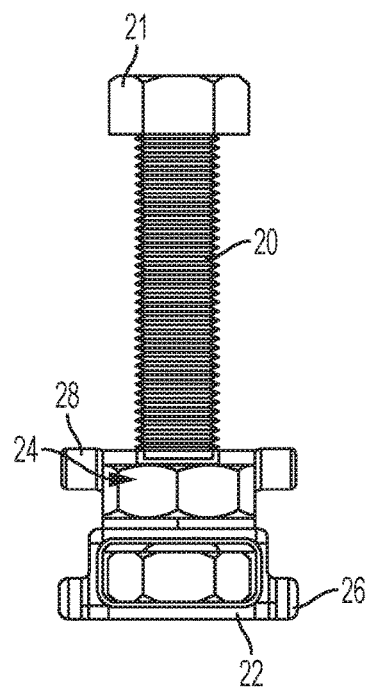
FIG. 10 is a side cut-away view of the screw assembly of FIG. 5.

The screw assembly 16 includes a screw 20 that is rotatably attached to a housing nut 22, which is pivotably attached to the pivot housing 12. The screw assembly 16 also includes a riding nut 24 that is movably attached to the screw 20. The screw assembly may include a handle 17 disposed at one end of the screw 20 to provide leverage for an operator to rotate the screw 20. In the illustrated embodiment, the handle 17 includes two outwardly extending shoulders 19. In other embodiments, the handle 17 may have a different configuration, or another structure may be substituted for the handle, for example, the nut head 21 of FIG. 10.

As illustrated in FIGS. 4-6 and 10, the housing nut 22 includes a housing pivot 26 and the riding nut 24 includes a riding pivot 28. In the illustrated embodiment, the housing pivot 26 and the riding pivot 28 are formed as a pair of outwardly extending hubs. In other embodiments, the housing pivot 26 and the riding pivot 28 may take the form of other pivotable connections. For example, in other embodiments, one of the housing pivot 26 and the riding pivot 28 may be formed as a hinge, or a non cylindrical projection. In any event, the housing pivot 26 is pivotable relative to the pivot housing 12. In the illustrated embodiment, the hubs of the housing pivot 26 are received in a pair of pivot hub receptacles 30, which are formed as blind bores. In other embodiments, the receptacles 30 may have virtually any other shape that is complimentary to the housing pivot 26 and that allows pivotable movement between the housing nut 22 and the pivot housing 12.

Figure 9A:
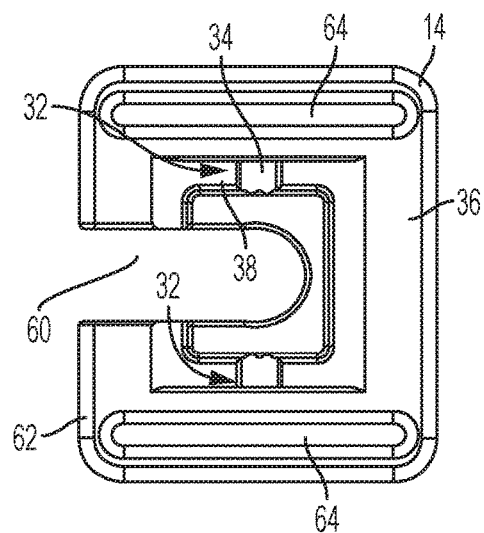
FIG. 9A is a top plan view of the strap carriage of the portable compact tourniquet of FIG. 1B.
Figure 9B:
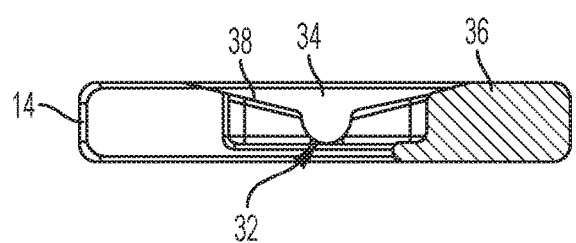
FIG. 9B is a side elevational view of the strap carriage of FIG. 9A.

Similar to the pivot hub receptacles 30 of the pivot housing 12, the strap carriage also includes strap hub receptacles 32, which are formed as blind bores having an opening 34 on a bottom side 36 of the strap carriage 14, as illustrated in FIGS. 9A and 9B. The strap carriage 12 also includes a guide ramp surface 38 that extends away from each strap hub receptacle 32.

When deploying the screw assembly 16 from the stowed position (FIG. 1A) to the deployed position (FIG. 1B), as the screw assembly 16 is pivoted (from the horizontal position in FIG. 1A to the vertical position in FIG. 1B) the riding pivot 28 slides along the guide ramp surface 38, which forces the strap carriage 14 slightly away from the pivot housing 14, until the riding pivot 28 seats in the strap hub receptacle 32, which allows the strap carriage 14 to contract slightly towards the pivot housing 12. The riding pivot 28 forms a press fit connection with the strap hub receptacle 32, thus allowing transmission of rotational motion of the screw assembly 16 to vertical motion of the strap carriage 14 (i.e., moves the strap carriage 14 away from the pivot housing 12 or towards the pivot housing 12). The strap carriage 14 moves freely along the screw 20 and when fitted with the riding nut 24, the strap carriage 14 moves vertically up the screw thread as the screw 20 is turned, which decreases the length of the tourniquet strap and thus decreases a circumference of the tourniquet strap encircling the limb, which increases pressure on the limb to stop blood flow to the injured region. When moving from the stowed configuration (FIG. 1A) to the deployed configuration (FIG. 1B), the guide ramp surfaces 36 prevent the riding pivots 28 on the riding nut 24 from becoming misaligned during the deployment process. When going from the deployed configuration (FIG. 1B) to the stowed configuration (FIG. 1A), as the screw assembly 16 folds forward, the riding pivots 28 disconnect from the strap hub receptacle 32 and the guide ramp surfaces 36 guide the riding pivots 28, and thus the screw assembly 16 into a stowed configuration to prevent misalignment. In other embodiments, the strap carriage 14 may include pockets and ribs to improve the strength-to-weight ratio of the strap carriage 14.

Figure 7:
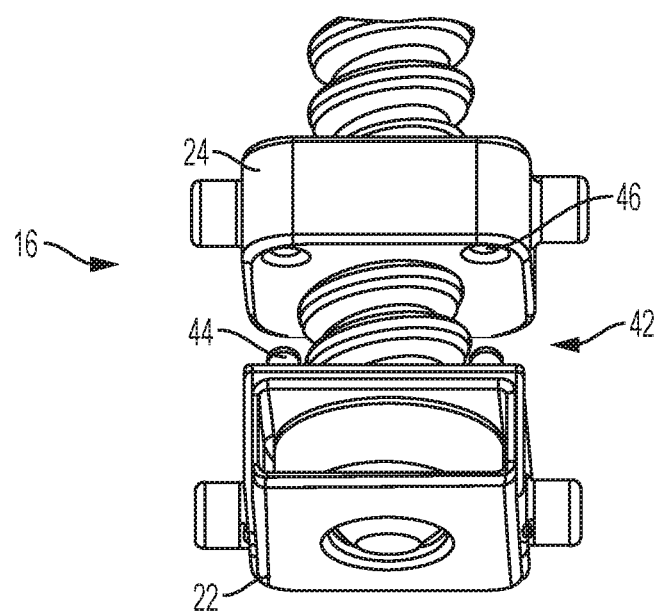
FIG. 7 is a bottom perspective view of a portion of the screw assembly of FIG. 5.

Turning now to FIG. 7, a centering mechanism 42 maintains alignment between the housing nut 22 and the riding nut 24 when the screw assembly 16 is rotated in one direction to bring the riding nut 24 (and thus the strap carriage 14) towards the pivot housing 12 for storage. In the illustrated embodiment, the centering mechanism 42 includes a mating boss 44 on the housing nut 22 and a mating pocket 46 on the riding nut 24. Additionally, the centering mechanism 42 prevents the riding nut 24 from freely turning on the screw 20 and becoming misaligned while the screw assembly 16 is folded into the stowed configuration.

Figure 8:
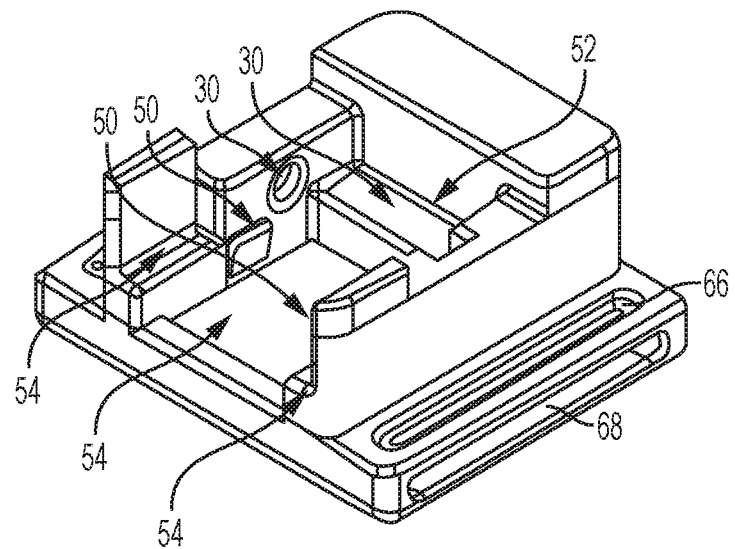
FIG. 8 is a perspective view of a pivot housing of the portable compact tourniquet of FIG. 1B.

Turning now to FIG. 8, the pivot housing 12 includes a pair of support tabs 50 for supporting a bottom of the housing nut 22. Additionally, the pivot housing 12 includes a shelf 52 for supporting a portion of the housing nut 22. When the screw assembly 16 is in the deployed position (e.g., FIG. 1B), the bottom of the housing nut 22 rests on top surfaces of the support tabs 50 and on a top surface of the shelf 52. The shelf 52 stabilizes the screw assembly when the tourniquet is in use and distributes vertical loading from the screw 20. When the screw assembly 16 is moved to the stowed configuration (e.g., FIG. 1A), the tabs are pressed, which releases the bottom surface of the housing nut 22 and allows the housing nut 22 (and thus the screw assembly 16) to pivot approximately 90 degrees. The pivot housing also includes a plurality of pockets 54. The bottom pocket 54 allows the riding nut 24 and housing nut 22 to rest within the pivot housing 12 when the screw assembly 16 is folded to the stowed position. The side pockets 54 hold a portion of the stopping nut 56 (FIGS. 5 and 6) as the screw assembly 16 is folded. The stopping nut 56 is fixed within the housing nut 22, the screw 20 being rotatably secured to the stopping nut 56. The screw 20 can rotate freely with the stopping nut 56 inside the nut housing 22.

Returning to FIGS. 5 and 6, the handle 17 provides the leverage for turning the screw assembly to provide tourniquet pressure. In the illustrated embodiment, as the handle 17 is turned clockwise, the screw 20 and stopping nut 56 spin freely, forcing the riding nut 24 to move vertically up the screw 20. In one embodiment, the screw 20 is sized to provide approximately 1.75-2.00 inches of travel for the riding nut 24, which is enough vertical travel to ensure that occlusion pressure is reached under all conditions.

Turning again to FIGS. 4 and 9A, the strap carriage 14 has a central slot 60 that extends through a front edge 62 of the strap carriage 14. The central slot 60 allows the screw 20 to fold into the stowed position. The strap carriage 14 also has pair of lateral slots 64 that are configured to receive a tourniquet strap. Similarly, the pivot housing 12 also has a pair of lateral slots 66 (FIG. 4) and a central slot 68 (FIG. 3) that are configured to receive a tourniquet strap.

Figure 11A:
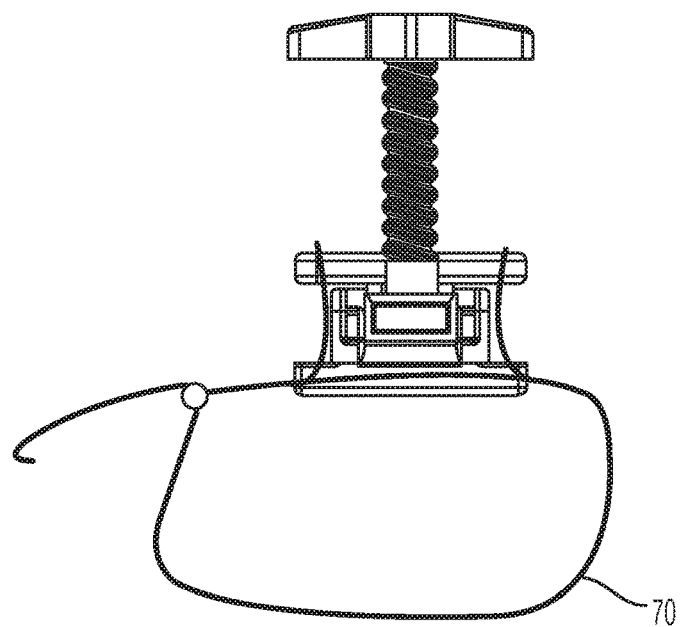
FIG. 11A is a side view of the portable compact tourniquet of FIG. 1B with a first embodiment of a tourniquet strap attached thereto.
Figure 11B:
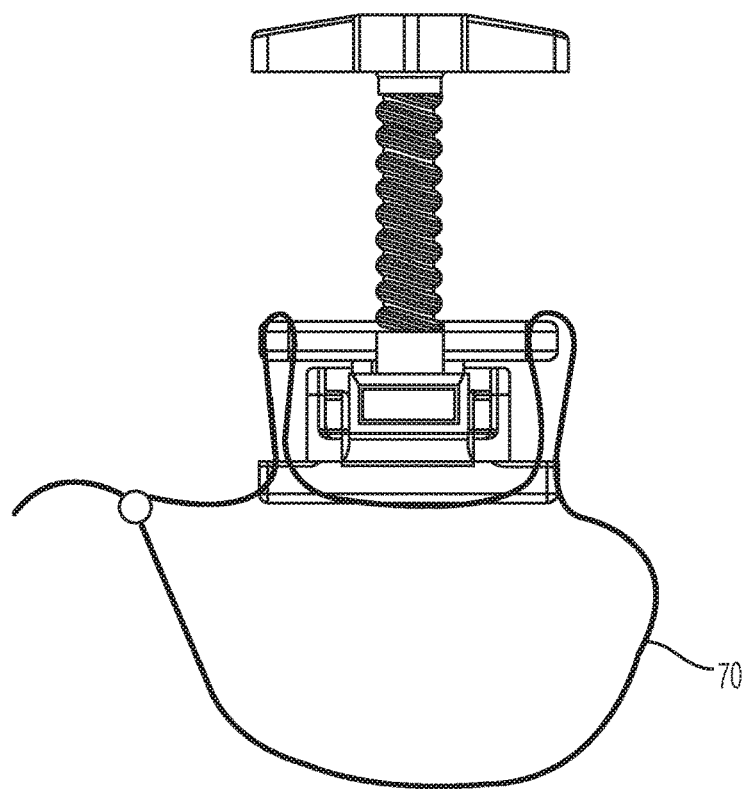
FIG. 11B is a side view of the portable compact tourniquet of FIG. 1B with a second embodiment of a tourniquet strap attached thereto.
Figure 13B:
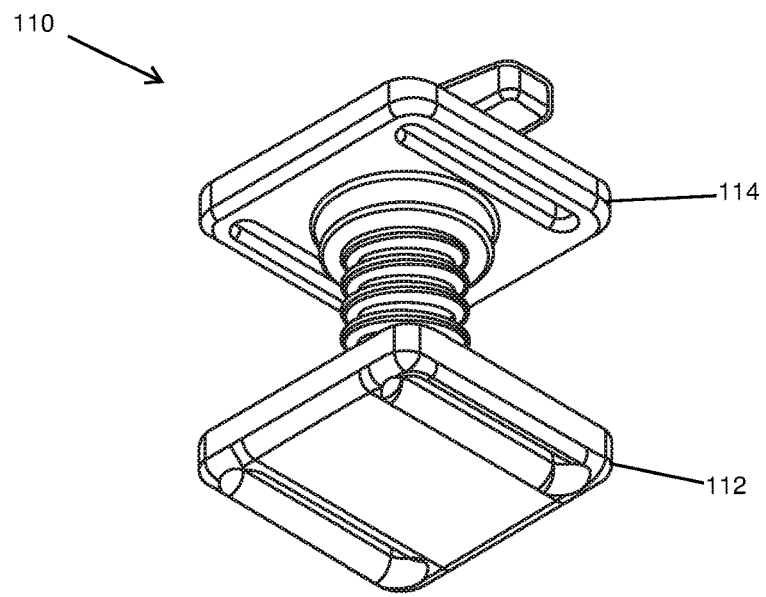
FIG. 13B is a bottom perspective view of the portable compact tourniquet of FIG. 12A.
Figures 14A, 14B, 14C:
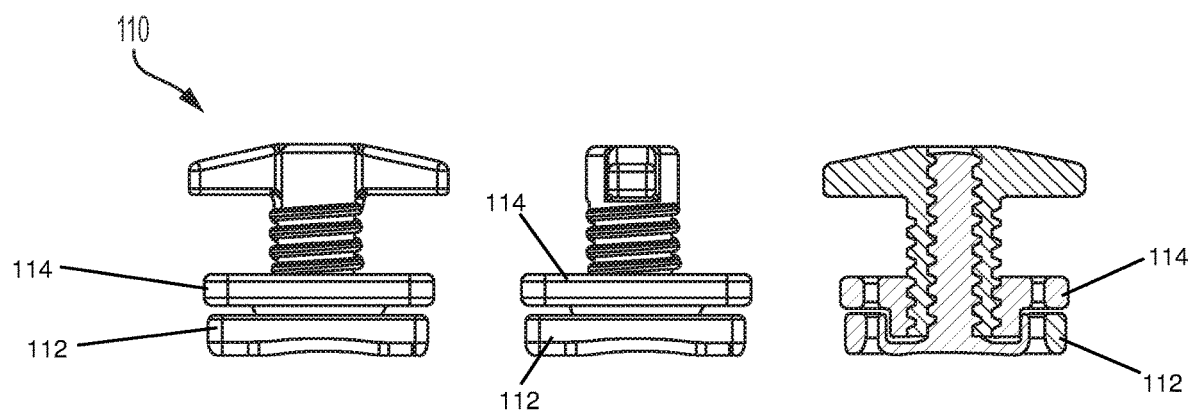
FIG. 14A is a front view of the second embodiment of a portable compact tourniquet, with a screw assembly in a retracted position.
FIG. 14B is a side view of the portable compact tourniquet of FIG. 14A.
FIG. 14C is a front cross-sectional view of the portable compact tourniquet of FIG. 14A.
Figure 15A:
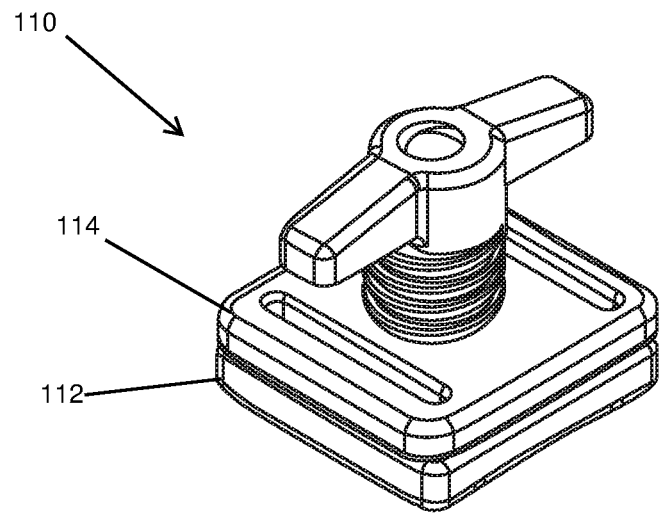
FIG. 15A is a top perspective view of the portable compact tourniquet of FIG. 14A.
Figure 15B:
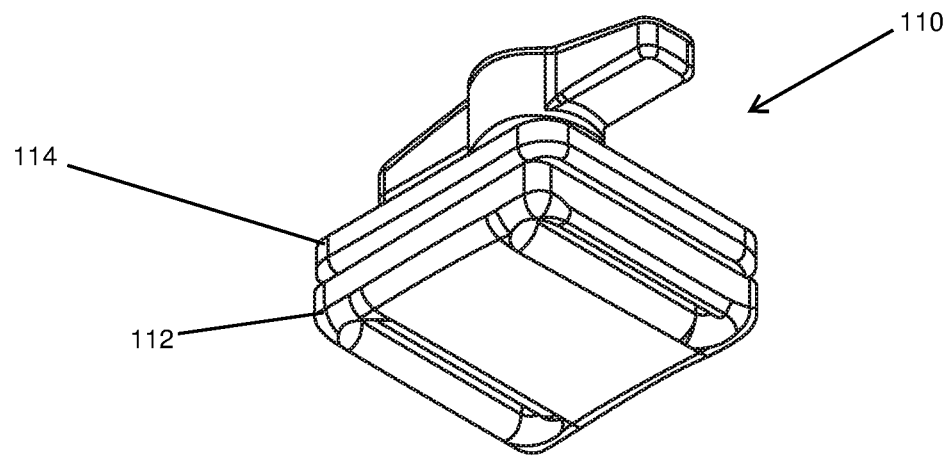
FIG. 15B is a bottom perspective view of the portable compact tourniquet of FIG. 14A.

FIGS. 11A and 11B illustrate two different tourniquet strap 70 configurations.

In one method of using the compact tourniquet, a user deploys the screw assembly 16 from the stowed position (FIG. 1A) into the deployed position FIG. 1B). The tourniquet strap 70 is then placed around the injured limb at a location between the injury and the trunk of the body. One end of the tourniquet strap 70 is pulled through a buckle built into the top of the strap carriage 14 until the tourniquet strap 70 is snug and tight on the limb. The handle 17 is turned (clockwise in the illustrated embodiment) until blood occlusion pressure is applied and blood flow out of the injury stops.

In another embodiment, a cinching mechanism for achieving initial tourniquet pressure may comprise a buckle on one end of the circumferential strap. The strap carriage 14 in this case would be attached to two fixed external straps (FIG. 11A).

In another embodiment, the entire strap assembly can be replaced with one tourniquet strap 70 that feeds through a bottom of the pivot housing 12, over one side of the strap carriage 14, back through the pivot housing 12, and over the other side of the strap carriage 14 (FIG. 11B).

In the embodiment of FIG. 11A, on the pivot housing 12, there are three strap slots, one of which goes across the entire bottom of the pivot housing 12 for the tourniquet strap 70. The other two slots serve as guides for the strap that feeds into the strap carriage 14. There is one external fixed strap that is fixed to the outer side of the tourniquet strap 70 at small distance from the side of the pivot housing 12. This fixed strap is then fed under and through the strap slot and up to be fixed through the strap carriage 14. One end of the tourniquet strap 70 feeds through a fixed loop on the other end of the tourniquet strap 70 and is then fed through the slot in the strap carriage 14. This slot will may include a passive cinching mechanism that will allow the tourniquet strap 70 to be initially tightened by pulling through on the end of the tourniquet strap 70.

The orientation and placement of the fixed strap and of tourniquet strap are configured to maximize the circumferential range that the tourniquet strap 70 can accommodate.

Turning now to FIGS. 12-15, a second embodiment of a compact tourniquet 110 is illustrated. Where similar elements to the embodiment of FIGS. 1-11 are illustrated, the elements of FIGS. 12-15 will be exactly 100 greater. For example, the compact tourniquet is labeled 10 in FIGS. 1-11 and is labeled 110 in FIGS. 12-15.

The portable compact tourniquet 110 if FIGS. 12-15 includes a screw base 112, a strap carriage 114 that is linearly translatable relative to the screw base 112, and a screw assembly 116 that is rotatably connected to the screw base 112. The screw assembly 116 includes a first screw 113 and a second screw 115 that is nested within the first screw 113. The first screw 113 has a larger diameter than the second screw 115. The first screw 113 has a hollow central bore 131 with female threads 133 and the female threads 133 cooperate with male threads 135 on an outer surface 137 of the second screw 115.

Similar to the embodiment of FIGS. 1-11, the screw assembly 116 may include a handle 117 disposed at one end of the first screw 113 to provide leverage for an operator to rotate the first screw 113. In the illustrated embodiment, the handle 117 includes two outwardly extending shoulders 119. In other embodiments, the handle 117 may have a different configuration, or another structure may be substituted for the handle.

Similar to the embodiment of FIGS. 1-11, the strap carriage 114 has pair of lateral slots 164 that are configured to receive a tourniquet strap. The screw base 112 also has a pair of lateral slots 166 that are configured to receive a tourniquet strap.

In other embodiments, cinching mechanisms (either in a buckle or in the strap carriage) may be replaced with a loop buckle or strap feed through slot. In these embodiments, the tourniquet strap is fixed with a combined hook and loop fastener on one side. This configuration allows the tourniquet to be initially tightened by pulling through and then affixing the strap to itself.

If increased torque is required, a larger handle may be used to provide more leverage. Another advantage of the disclosed compact tourniquets is that a user doesn't need to constantly apply the torque to hold the pressure, but rather, the screw assembly includes a locking device, such as a ratchet, which prevents the screw assembly from turning in a loosening direction unless the lock is released. This also allows fine-tuning of the occlusion pressure through tightening at any incremental turning of the screw.

The disclosed compact tourniquets are easy to use, generate great mechanical advantage in tightening, and utilize wide tourniquet bands for less pain and more effective occluding pressures during application. The disclosed tourniquets are also easily deployable and operable with one hand while operating solely on mechanical power generated by the user, so that a source of electrical power is not needed. Furthermore due to the compact nature the disclosed tourniquets are easily portable and generally light weight so that they may be deployed almost anywhere.

While the present invention has been described with respect to a particular embodiment of the present invention, this is by way of illustration for purposes of disclosure rather than to confine the invention to any specific arrangement as there are various alterations, changes, deviations, eliminations, substitutions, omissions and departures which may be made in the particular embodiment shown and described without departing from the scope of the claims.

What is claimed is:

1. A portable compact tourniquet comprising:
  a pivot housing, the pivot housing including a pair of lateral slots;
  a strap carriage that is linearly translatable relative to the pivot housing;
  a tourniquet strap attached to the strap carriage and the pair of lateral slots; and
  a screw assembly that is pivotably attached to the pivot housing,
  wherein in a deployed condition, the screw assembly moves the strap carriage away from the pivot housing when the screw assembly is operated.

2. The portable compact tourniquet of claim 1, wherein the screw assembly comprises a screw that is rotatably attached to a housing nut, which is pivotably attached to the pivot housing.

3. The portable compact tourniquet of claim 2, wherein the screw assembly further comprises a riding nut that is movably attached to the screw.

4. The portable compact tourniquet of claim 3, wherein a centering mechanism orients the housing nut and the riding nut relative to one another in a closed position.

5. The portable compact tourniquet of claim 4, wherein the centering mechanism includes a mating boss on one of the riding nut and the housing nut and a mating pocket on the other of the housing nut and the riding nut.

6. The portable compact tourniquet of claim 1, wherein the strap carriage includes a pair of strap hub receptacles.

7. The portable compact tourniquet of claim 6, wherein the strap hub receptacles are blind bores having an opening on a bottom side of the strap carriage.

8. The portable compact tourniquet of claim 7, wherein the strap carriage includes a guide ramp surface that extends away from each strap hub receptacle.

9. The portable compact tourniquet of claim 1, wherein the screw assembly includes a handle.

10. The portable compact tourniquet of claim 9, wherein the handle includes two outwardly extending shoulders.

11. A portable compact tourniquet comprising:
  a pivot housing;
  a strap carriage that is linearly translatable relative to the pivot housing;
  a tourniquet strap attached to the strap carriage; and
  a screw assembly that is pivotably attached to the pivot housing,
  wherein in a deployed condition, the screw assembly moves the strap carriage away from the pivot housing when the screw assembly is operated,
  wherein the screw assembly comprises a screw that is rotatably attached to a housing nut, which is pivotably attached to the pivot housing, and a riding nut that is movably attached to the screw, and
  wherein the housing nut includes a housing pivot and the riding nut includes a riding pivot.

12. The portable compact tourniquet of claim 11, wherein the screw assembly further comprises a stopping nut that is fixed within the housing nut, the screw being rotatably secured to the stopping nut.

13. The portable compact tourniquet of claim 11, wherein one of the housing pivot and the riding pivot includes a pair of outwardly extending hubs.

14. The portable compact tourniquet of claim 11, wherein the pivot housing includes a pair of pivot hub receptacles.

15. The portable compact tourniquet of claim 14, wherein the pivot hub receptacles are blind bores.

16. A portable compact tourniquet comprising:
  a pivot housing;
  a strap carriage that is linearly translatable relative to the pivot housing;
  a tourniquet strap attached to the strap carriage; and
  a screw assembly that is pivotably attached to the pivot housing, the screw assembly including a screw that is rotatably attached to a housing nut, which is pivotably attached to the pivot housing,
  wherein in a deployed condition, the screw assembly moves the strap carriage away from the pivot housing when the screw assembly is operated, and
  wherein the pivot housing includes a pair of support tabs for supporting a bottom of the housing nut.

17. A portable compact tourniquet comprising:
  a pivot housing;
  a strap carriage that is linearly translatable relative to the pivot housing;
  a tourniquet strap attached to the strap carriage; and
  a screw assembly that is pivotably attached to the pivot housing, the screw assembly including a screw that is rotatably attached to a housing nut, which is pivotably attached to the pivot housing,
  wherein in a deployed condition, the screw assembly moves the strap carriage away from the pivot housing when the screw assembly is operated, and
  wherein the pivot housing includes a shelf for receiving a portion of the housing nut.

18. A portable compact tourniquet comprising:
  a screw base, the screw base including a pair of lateral slots;
  a strap carriage that is linearly translatable relative to the screw base;
  a tourniquet strap attached to the strap carriage and the pair of lateral slots; and
  a screw assembly that is rotatably connected to the screw base, the screw assembly including a first screw and a second screw that is nested within the first screw.

19. The portable compact tourniquet of claim 18, wherein the first screw has a larger diameter than the second screw.

20. The portable compact tourniquet of claim 18, wherein the first screw has a hollow central bore with female threads, the female threads cooperating with male threads on an outer surface of the second screw.

* * * * *

UNITED STATES PATENT AND TRADEMARK OFFICE
CERTIFICATE OF CORRECTION

PATENT NO. : 10,695,071 B2
APPLICATION NO. : 15/866528
DATED : June 30, 2020
INVENTOR(S) : Kevin R. Ward et al.

Page 1 of 1

It is certified that error appears in the above-identified patent and that said Letters Patent is hereby corrected as shown below:

On the Title Page

Item (60), Line 1, "62/455,205," should be -- 62/445,205, --.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*